United States Patent
Bisgård-Frantzen et al.

(10) Patent No.: US 7,341,858 B2
(45) Date of Patent: *Mar. 11, 2008

(54) FUNGAMYL-LIKE ALPHA-AMYLASE VARIANTS

(76) Inventors: Henrik Bisgård-Frantzen, Elmevænget 8B, DK-2880 Bagsværd (DK); Allan Svendsen, Overdamsvej 13, DK-2970 Hørsholm (DK); Sven Pedersen, Emil Reesens Vej 9, DK-2820 Gentofte (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/633,385

(22) Filed: Dec. 4, 2006

(65) Prior Publication Data

US 2007/0128313 A1     Jun. 7, 2007

Related U.S. Application Data

(60) Division of application No. 10/820,200, filed on Apr. 7, 2004, now Pat. No. 7,160,710, which is a continuation of application No. 09/710,339, filed on Nov. 9, 2000, now Pat. No. 7,005,288.

(60) Provisional application No. 60/165,786, filed on Nov. 16, 1999.

(30) Foreign Application Priority Data

Nov. 10, 1999   (DK)   .............. 1999 01617

(51) Int. Cl.
    *C12N 9/30*     (2006.01)
    *C12N 15/00*    (2006.01)
    *C07K 1/00*     (2006.01)
    *C12P 19/14*    (2006.01)
    *C12P 7/02*     (2006.01)

(52) U.S. Cl. .......... 435/203; 530/350; 435/99; 435/155; 435/252.3; 435/320.1

(58) Field of Classification Search ........... 435/203, 435/99, 155, 252.3, 320.1; 530/350
See application file for complete search history.

(56) References Cited

U.S. PATENT DOCUMENTS

| 5,731,280 A | 3/1998  | Nielsen et al.     |
| 6,136,553 A | 10/2000 | Christianson et al. |

FOREIGN PATENT DOCUMENTS

| WO | WO 90/11352 | 10/1990 |
| WO | WO 95/10603 | 4/1995  |
| WO | WO 95/26397 | 10/1995 |
| WO | WO 96/23873 | 8/1996  |
| WO | WO 96/23874 | 8/1996  |

OTHER PUBLICATIONS

Korman, David R. et al; Current Genetics, vol. 17, pp. 203-212 (1990).
Ichiro Shibuya et al; Bioscience Biotechnology Biochemistry, vol. 56, part 2, pp. 174-179 (1992).
Matsuura et al; J. Biochem, vol. 95, part 3, pp. 697-702 (1984).

*Primary Examiner*—Maryam Monshipouri

(57) ABSTRACT

The invention relates to a variant of a parent Fungamyl-like fungal alpha-amylase, which exhibits improved thermal stability at acidic pH suitable for, e.g., starch processes.

31 Claims, No Drawings

FUNGAMYL-LIKE ALPHA-AMYLASE VARIANTS

CROSS-REFERENCE TO RELATED APPLICATIONS

This application is a divisional of U.S. application Ser. No. 10/820,200 filed Apr. 7, 2004, now U.S. Pat. No. 7,160,710, which is a continuation of U.S. application Ser. No. 09/710,339, filed Nov. 09, 2000, now U.S. Pat. No. 7,005,288, which claims, under 35 U.S.C. 119, the benefit of U.S. provisional application Ser. No. 60/165,786, filed Nov. 16, 1999, and priority from Danish application no. PA 1999 01617 filed Nov. 10, 1999, the contents of which are fully incorporated herein by reference.

FIELD OF THE INVENTION

The present invention relates to alpha-amylase variants (mutants) of Fungamyl™-like alpha-amylases, in particular with improved thermal stability at acidic pH. The invention also relates to the use of such variants.

BACKGROUND OF THE INVENTION

Alpha-Amylases (alpha-1,4-glucan-4-glucanohydrolases, EC. 3.2.1.1) constitute a group of enzymes which catalyze hydrolysis of starch and other linear and branched 1,4-glucosidic oligo- and polysaccharides.

There is a very extensive body of patent and scientific literature relating to this industrially very important class of enzymes. A number of alpha-amylase referred to as "Termamyl®-like alpha-amylases" and variants thereof are known from, e.g., WO 90/11352, WO 95/10603, WO 95/26397, WO 96/23873 and WO 96/23874. Termamyl-like alpha-amylases are very thermostable and therefore suitable for processes carried out at high temperatures such as starch liquefaction in dextrose production processes.

Another group of alpha-amylases are referred to as "Fungamyl®-like alpha-amylases", which are alpha-amylases related to the alpha-amylase derived from Aspergillus oryzae (and shown in SEQ ID NO: 1). These Fungamyl-like alpha-amylases have a relatively low thermostability (the commercial product sold under the tradename FUNGAMYL™ by Novo Nordisk, Denmark, has a optimum around 55° C.) and is therefore not suitable for processes carried out at high temperatures. Fungamyl-like alpha-amylases are today used for making syrups for, e.g., the brewing industry. Such processes are operated at around 60° C. resulting in that usually in the range of double the enzyme dosage must be used to compensate for the low thermostability. Further, at 55° C. infection problems may occur.

As such processes today furthermore are carried out at a pH of 5.5, instead of, e.g., pH 4.5, pH adjustment and addition of Sodium to the syrups are necessitated.

Therefore, it would be advantageous to provide a Fungamyl-like alpha-amylase with increased thermostability preferably at an acidic pH.

BRIEF DISCLOSURE OF THE INVENTION

The object of the present invention is to provide Fungamyl-like alpha-amylase variant, in particular with improved thermostablility especially at acidic pH.

The term "an alpha-amylase variant with improved thermostability" means in the context of the present invention an alpha-amylase variant, which has a higher thermostability than corresponding parent alpha-amylases. The determination of thermostability is described below in the Materials and Method section.

The inventors have provided improved Fungamyl-like alpha-amylase variants as will be described further below.

DETAILED DISCLOSURE OF THE INVENTION

A goal of the work underlying the present invention was to improve the thermal stability, in particular at acidic pH of Fungamyl-like alpha-amylases.

Identifying Positions and/or Regions to be Mutated to Obtain Improved Thermostability Molecular dynamics (MD) simulations indicate the mobility of the amino acids in the protein structure (see McCammon, J A and Harvey, S C., (1987), "Dynamics of proteins and nucleic acids". Cambridge University Press.). Such protein dynamics are often compared to the crystallographic B-factors (see Stout, G H and Jensen, L H, (1989), "X-ray structure determination", Wiley) or the B-factors themselves. By running the MD simulation at different protonation states of the titrateable residues, the pH related mobility of residues are simulated. Regions having the highest mobility or flexibility (here isotropic fluctuations) are selected for random mutagenesis. It is here understood that the high mobility found in certain areas of the protein, can be thermally improved by substituting residues in these residues. The substitutions are directed against residues that have bigger side-chains and/or which have capability of forming improved contacts to residues in the near environment. The parent Fungamyl® alpha-amylase backbone shown in SEQ ID NO: 2 derived from Aspergillus oryzae was used for the MD simulation.

Regions found by Molecular dynamics (MD) simulations or B factor examination (as enclosed to the Protein Data Base (PDB)(www.rcsb.org) file 6TAA (Swift, H. J., Brady, L., Derewenda, Z. S., Dodson, E. J., Dodson, G. G., Turkenburg, J. P., Wilkinson, A. J.: Structure and molecular model refinement of Aspergillus oryzae (TAKA) alpha-amylase: an application of the simulated-annealing method. Acta Crystallogr B 47 pp. 535 (1991)) to be suitable for mutation when wanting to obtain, in particular increased thermal stability are the following:

Region 98-110,
Region 150-160,
Region 161-167,
Region 280-288,
Region 448-455,
Region 468-475.

The above regions are show to be flexible. Making said regions more rigid would make the molecule more thermostable.

Accordingly, in a first aspect the present invention relates to a variant of a parent Fungamyl-like alpha-amylase comprising one or more mutations in the regions and positions described further below.

Nomenclature

In the present description and claims, the conventional one-letter and three-letter codes for amino acid residues are used. For ease of reference, alpha-amylase variants of the invention are described by use of the following nomenclature:

Original amino acid(s):position(s):substituted amino acid(s)

According to this nomenclature, for instance the substitution of alanine for asparagine in position 30 is shown as:

Ala30Asn or A30N a deletion of alanine in the same position is shown as:
Ala30* or A30* and insertion of an additional amino acid residue, such as lysine, is shown as:
Ala30AlaLys or A30AK A deletion of a consecutive stretch of amino acid residues, such as amino acid residues 30-33, is indicated as (30-33)* or Δ(A30-N33).

Where a specific alpha-amylase contains a "deletion" in comparison with other alpha-amylases and an insertion is made in such a position this is indicated as:
*36Asp or *36D for insertion of an aspartic acid in position 36

Multiple mutations are separated by plus signs, i.e.:
Ala30Asp +Glu34Ser or A30N+E34S representing mutations in positions 30 and 34 substituting alanine and glutamic acid for asparagine and serine, respectively. Multiple mutations may also be separated as follows, i.e., meaning the same as the plus sign:
Ala30Asp/Glu34Ser or A30N/E34S When one or more alternative amino acid residues may be inserted in a given position it is indicated as
A30N,E or
A30N or A30E Furthermore, when a position suitable for modification is identified herein without any specific modification being suggested, it is to be understood that any amino acid residue may be substituted for the amino acid residue present in the position.

Thus, for instance, when a modification of an alanine (A) in position 30 is mentioned, but not specified, or specified as "A30X", it is to be understood that the alanine may be deleted or substituted for any other amino acid, i.e., any one of: R,N,D,A,C,Q,E,G,H,I,L,K,M,F,P,S,T,W,Y,V.

Fungamyl-Like Alpha-Amylases

Parent Fungamyl-like alpha-amylase are according to the present invention enzymes with alpha-amylase activity which either have at least 60%, preferably at least 70%, more preferably at least 80%, even more preferably at least 90%, even more preferably at least 93%, even more preferably at least 95%, even more preferably at least 97%, even more preferably at least 99% identity to the DNA sequence shown in SEQ ID NO: 1 encoding the alpha-amylase and/or the mature part of the alpha-amylase protein sequence shown in SEQ ID NO: 2 and/or structurally resembles the three-dimensional structure of the FUNGAMYL® alpha-amylase shown in SEQ ID NOS: 1 and 2, and further disclosed in the Protein Data Base (PDB) (www.rcsb.org) file 6TAA (Swift, H. J., Brady, L., Derewenda, Z. S., Dodson, E. J., Dodson, G. G., Turkenburg, J. P., Wilkinson, A. J.: Structure and molecular model refinement of *Aspergillus oryzae* (TAKA) alpha-amylase: an application of the simulated-annealing method. *Acta Crystallogr B* 47 pp. 535 (1991) and/or is encoded by a DNA sequence, which hybridizes to the part of the DNA sequence shown in SEQ ID NO: 1 encoding the mature part of the alpha-amylase shown in SEQ ID NO: 2 of the present specification.

Specific examples of such alpha-amylases covered by the definition "Fungamyl-like alpha-amylases" include the *Aspergillus oryzae* TAKA alpha-amylase (EP 238 023) and shown in SEQ ID NO: 2, and the *A. niger* alpha-amylase disclosed in EP 383,779 B2 (section (see also the cloning of the *A. niger* gene in Example 1).

In an embodiment the Fungamyl-like alpha-amylase is derived from a fungal organism, in particular of the genus *Aspergillus*, in particular *A oryzae* or *A. niger*.

Commercially Available Parent Fungamyl-Like Alpha-Amylases

Commercially available parent Fungamyl-like alpha-amylases include Fungamyl® (from Novo Nordisk, Denmark). Fungamyl® is a fungal alpha-amylase obtained from a selected strain of *Aspergillus oryzae*. In the starch industry, Fungamyl® is used for production of high maltose syrups, 45-60% maltose (2-7% glucose) or high conversion syrups, DE 60-70, 35-43% glucose, 30-37% maltose. Other commercial fungal alpha-amylases include Clarase™ (from Genencor Int., USA) derived from *Aspergillus oryzae*; and Maltamyl™ (from Enzyme Biosystems) derived from *Aspergillus niger*.

In the brewing industry, FUNGAMYL® (and similar products) is added during fermentation in order to increase fermentability of the wort.

In the alcohol industry, FUNGAMYL® may be used for liquefaction of starch in a distillery mash if the existing equipment favors low-temperature liquefaction (55-60° C.). FUNGAMYL® (and similar products) is also used for baking and can be used for all types of bread and baked products. For instance FUNGAMYL® improves the dough stability, result in greater bread volume, improves crumb softness and give the crust a darker color.

Alpha-Amylase Variants of the Invention

In the first aspect the invention relates to a variant of a parent Fungamyl-like alpha-amylase comprising one or more mutation(s) in the following positions(s) or region(s) in the amino acid sequence shown in NO: 2:
Region 98-110,
Region 150-160,
Region 161-167;
Region 280-288,
Region 448-455,
Region 468-475, and/or in a corresponding position or region in a homologous Fungamyl-like alpha-amylase which displays at least 60% identity with the amino acid sequences shown in SEQ ID NO: 2. In an embodiment the region mutated is Region 98-110.

In an embodiment the region mutated is Region 98-110, more specifically one or more of the following positions: 98, 99, 100, 101, 102, 103, 104, 105, 106, 107, 108, 109, 110.

Specific substitutions are
98X, preferably T;
99X, preferably T;
100F,Y,W,I,M; preferably Y;
101R;
102S,T,V;
103I,F,V, preferably I;
104T,V,I;
105X, preferably A;
106V,L,N,D,Q,E, preferably V;
107V,I,M;
108Y,R,K;
109D,N,Q;
110Q.

In an embodiment the region mutated is Region 150-160, more specifically one or more of the following positions: 150, 151, 152, 153, 154, 155, 156, 157, 158, 159, 160.

Specific substitutions are
151Y,Q,L,I,R, preferably Y;
152V,L;

153T,N,S, preferably S;
154L,Y,V,T,S, preferably L;
155F,N,L;
156X, preferably D,N,S,T;
157S,T,N;
158E,Y
159X, preferably S,A;
160X, preferably N;

In an embodiment the region mutated is Region 161-167, more specifically one or more of the following positions: 161, 162, 163, 164, 165, 166, 167.

Specific substitutions are
161I,S,T;
162D,N,Q,Y;
163E,Q,N;
166V,F,Y,I,S,T,prefeably V,F,Y;
167A;

In an embodiment the region mutated is Region 280-288, more specifically one or more of the following positions: 280, 281, 282, 283, 284, 285, 286, 287, 288.

Specific substitutions are
280Q,Y,R;
281X, preferably T,A;
282X, preferably S,T;
285L,N;
286X, preferably D;
287V,S,A;
288N,F,Y,E,D, preferably N;

In an embodiment the region mutated is Region 448-455 more specifically one or more of the following positions: 448, 449, 450, 451, 452, 453, 454, 455.

Specific substitutions are:
448X, preferably A,L,Y,S,T;
449x, preferably L,V,S,T;
450I,T,L;
452I,L;
454I,L;
455D,E,S,T.

In an embodiment the region mutated is Region 468-475 more specifically one or more of the following positions: 468, 469, 470, 471, 472, 473, 474, 475.

Specific substitutions are:
468F,Y,H;
469E,D,Q,N;
470X, preferably A,S,T;
471N,T,K,R,F,Y preferably N,T,Y;
472R;
473L,N,Y;
475X, preferably T,R.

Improved Stability at Acidic pH

One object of the invention is to make the Fungamyl-like alpha-amylase more acidic in comparison to the parent alpha-amylase (i.e., corresponding un-mutated alpha-amylase).

That a Fungamyl-like alpha-amylase variant is more acidic than the parent Fungamyl-like alpha-amylase means that the stability at acidic pH is higher that for the corresponding parent alpha-amylase. That the amylase is more acidic may be determined as described in the "Materials & Methods" section.

The term "acidic pH" means at least in the context of the present invention a pH in the range from 4-6, such as 4-5, in particular 4.2-4.7.

Providing more acidic fungal alpha-amylases are desired, because it opens up for the possibility of using the fungal alpha-amylase variant together with or simultaneously with a suitable glucoamylase, e.g., during the (dextrinazation) saccharification step in starch processes.

Thermal Stability

One object of the invention is to provide a more thermostable Fungamyl-like alpha-amylase.

That a Fungamyl-like alpha-amylase variant is more thermostable than the parent Fungamyl-like alpha-amylase means that the temperature optimum has been pushed towards a higher temperature. That the amylase is more thermostable may be determined as described in the "Materials & Methods" section.

Providing more thermostable fungal alpha-amylases is desired because it renders a more efficient and/or faster liquefaction step possible. Further, the liquefaction temperature is less sensitive and may even be increased (i.e., less cooling necessary. Further, the risk of infection is also reduced.

It is to be understood that variants of the invention may have both a more stable at acidic pH and be more thermostable, in particular at acidic pH.

Homology (Identity)

The homology (identity) referred to above of the parent alpha-amylase is determined as the degree of identity between two protein or DNA sequences indicating a derivation of the first sequence from the second. The homology (identity) may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, p. 443-453). The (default) GAP creation penalty is 5.0 and the GAP extension penalty of 0.3, respectively, for nucleic acidic sequence comparison; and (default) GAP creation penalty is 3.0 and GAP extension penalty of 0.1, respectively, for protein sequence comparison. GAP uses the method of Needleman and Wunsch, (1970), J. Mol. Biol. 48, p.443-453, to make alignments and to calculate the identity.

Using GAP with the above settings for polypeptide or DNA sequence comparison a parent Fungamyl-like alpha-amylase has a degree of identity preferably of at least 60%, such as 70%, at least 80%, at least 90%, more preferably at least 95%, more preferably at least 97%, and most preferably at least 99% with the mature part of the amino acid sequence shown in SEQ ID NO: 2 and encoding part of the DNA sequence shown in SEQ ID NO: 1.

In a preferred embodiment the variant of the invention has improved thermal stability, in particular at acidic pH.

Hybridisation

Oligonucleotide probes used in the characterisation of the Fungamyl-like alpha-amylase may suitably be prepared on the basis of the full or partial nucleotide or amino acid sequence of the alpha-amylase in question.

Suitable conditions for testing hybridisation involve presoaking in 5×SSC and prehybridizing for 1 hour at ~40° C. in a solution of 20% formamide, 5× Denhardt's solution, 50 mM sodium phosphate, pH 6.8, and 50 mg of denatured sonicated calf thymus DNA, followed by hybridisation in the same solution supplemented with 100 mM ATP for 18 hours at 40° C., followed by three times washing of the filter in 2×SSC, 0.2% SDS at 40° C. for 30 minutes (low stringency), preferred at 50° C. (medium stringency), more preferably at 65° C. (high stringency), even more preferably at 75° C. (very high stringency). More details about the hybridisation method can be found in Sambrook et al., Molecular_Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant, which is the result of a modification (insertion, substitution, deletion) of one or more amino acid residues of the naturally occurring alpha-amylase.

Cloning a DNA sequence encoding an Fungamyl-like alpha-amylaseCloning a DNA sequence encoding an a-amylaseCloning a DNA sequence encoding an a-amylaseCloning a DNA sequence encoding an a-amylaseCloning a DNA sequence encoding an a-amylaseCloning a DNA sequence encoding an a-amylaseCloning a DNA sequence encoding an a-amylaseCloning a DNA sequence encoding an a-amylase The DNA sequence encoding a parent Fungamyl-like alpha-amylase may be isolated from any cell or microorganism producing alpha-amylases, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, labeled oligonucleotide probes may be synthesized and used to identify alpha-amylase-encoding clones from a genomic library prepared from the organism in question. Alternatively, a labelled oligonucleotide probe containing sequences homologous to another known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase (i.e., maltose), thereby allowing clones expressing the alpha-amylase to be identified.

Alternatively, the DNA sequence encoding the enzyme may be prepared synthetically by established standard methods, e.g. the phosphoroamidite method described S. L. Beaucage and M. H. Caruthers, (1981), Tetrahedron Letters 22, p. 1859-1869, or the method described by Matthes et al., (1984), EMBO J. 3, p. 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and CDNA origin or mixed genomic and CDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., (1988), Science 239, pp. 487-491.

Site-Directed Mutagenesis

Once a Fungamyl-like alpha-amylase-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984), Biotechnology 2, p. 646-639. U.S. Pat. No. 4,760,025 disclose the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into α-amylase-encoding DNA sequences is described in Nelson and Long, (1989), Analytical Biochemistry 180, p. 147-151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localized or region-specific random mutagenesis in at least three parts of the gene translating to the amino acid sequence shown in question, or within the whole gene.

The random mutagenesis of a DNA sequence encoding a parent glucoamylase may be conveniently performed by use of any method known in the art.

In relation to the above, a further aspect of the present invention relates to a method for generating a variant of a parent Fungamyl-like alpha-amylase, wherein the variant exhibits increased thermal stability, especially at acidic pH, relative to the parent, the method comprising:

(a) subjecting a DNA sequence encoding the parent Fungamyl-like alpha-amylase to random mutagenesis,
(b) expressing the mutated DNA sequence obtained in step (a) in a host cell, and
(c) screening for host cells expressing an alpha-amylase variant which has an altered property (i.e., thermal stability) relative to the parent Fungamyl-like alpha-amylase.

Step (a) of the above method of the invention is preferably performed using doped primers, as described in the working examples herein (vide infra).

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one, which induces transitions, transversions, inversions, scrambling, deletions, and/or insertions.

Examples of a physical or chemical mutagenizing agent suitable for the present purpose include ultraviolet (UV) ir-radiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions, which are to be changed. The doping or spiking may be done so that codons for unwanted amino acids are avoided. The doped or spiked oligonucleotide can be incorporated into the DNA encoding the glucoamylase enzyme by any published technique, using, e.g., PCR, LCR or any DNA polymerase and ligase as deemed appropriate.

Preferably, the doping is carried out using "constant random doping", in which the percentage of wild type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program which, inter alia, ensures that introduction of stop codons is avoided.

When PCR-generated mutagenesis is used, either a chemically treated or non-treated gene encoding a parent glucoamylase is subjected to PCR under conditions that increase the mis-incorporation of nucleotides (Deshler 1992; Leung et al., Technique, Vol.1, 1989, pp. 11-15).

A mutator strain of E. coli (Fowler et al., Molec. Gen. Genet., 133, 1974, pp. 179-191), S. cereviseae or any other microbial organism may be used for the random mutagenesis of the DNA encoding the glucoamylase by, e.g., transforming a plasmid containing the parent glycosylase into the mutator strain, growing the mutator strain with the plasmid and isolating the mutated plasmid from the mutator strain. The mu-ta-ted plasmid may be subsequently transformed into the expression organism.

The DNA sequence to be mutagenized may be conveniently present in a genomic or cDNA library prepared from an organism expressing the parent glucoamylase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram-negative bacteria such as *E. coli*.

The mutated DNA sequence may further comprise a DNA sequence encoding functions permitting expression of the mutated DNA sequence.

Localized Random Mutagenesis

The random mutagenesis may be advantageously localized to a part of the parent alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative methods for providing variants of the invention include gene shuffling, e.g., as described in WO 95/22625 (from Affymax Technologies N.V.) or in WO 96/00343 (from Novo Nordisk A/S), or other corresponding techniques resulting in a hybrid enzyme comprising the mutation(s), e.g., substitution(s) and/or deletion, in question.

Expression of Alpha-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

Expression Vector

The recombinant expression vector carrying the DNA sequence encoding an alpha-amylase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

Promoter

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell.

Examples of suitable promoters for directing the transcription of the DNA sequence encoding an alpha-amylase variant of the invention, especially in a bacterial host, are the promoter of the lac operon of *E.coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, the TPI (triose phosphate isomerase) promoter from *S. cerevisiae* (Alber et al. (1982), J. Mol. Appl. Genet 1, p. 419-434, *Rhizo-mucor* miehei aspartic proteinase, *A. niger* neutral alpha-amylase, *A. niger* acid stable alpha-amylase, *A. niger* glucoamylase, *Rhizo-mucor* miehei lipase, *A. oryzae*alkaline protease, *A. oryzae*triose phosphate isomerase or *A. niulans* acetamidase.

Expression Vector

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

The procedures used to ligate the DNA construct of the invention encoding a glucoamylase variant, the promoter, terminator and other elements, respectively, and to insert them into suitable vectors containing the information necessary for replication, are well known to persons skilled in the art (cf., for instance, Sambrook et al., *Molecular Cloning: A Laboratory Manual*, 2nd Ed., Cold Spring Harbor, 1989).

Host Cells

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are Gram-positive bacteria such as *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium*, *Bacillus thuringiensis*, or *Streptomyces lividans* or *Streptomyces murinus*, or gram-negative bacteria such as *E.coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g., *Saccharomyces cerevisiae*.

The host cell may also be a filamentous fungus, e.g., a strain belonging to a species of *Aspergillus*, most preferably *Aspergillus oryzae* or *Aspergillus niger*, or a strain of *Fusarium*, such as a strain of *Fusarium oxysporium*, *Fusarium graminearum* (in the perfect state named *Gribberella zeae*, previously *Sphaeria zeae*, synonym with *Gibberella roseum* and *Gibberella roseum* f. sp. cerealis), or *Fusarium sulphureum* (in the prefect state named *Gibberella puricaris*, synonym with *Fusarium trichothecioides*, *Fusarium bactridioides*, *Fusarium sambucium*, *Fusarium roseum*, and *Fusarium roseum* var. *graminearum*), *Fusarium cerealis* (synonym with *Fusarium crokkwellnse*), or *Fusarium venenatum*.

In a preferred embodiment of the invention the host cell is a protease deficient or protease minus strain. This may for instance be the protease deficient strain of the genus *Aspergillus*, in particular a strain of *A. oryzae*, such as *A. oryzae* JaL125 having the alkaline protease gene named "alp" deleted. This strain is described in WO 97/35956 (Novo Nordisk).

Filamentous fungi cells may be transformed by a process involving protoplast formation and transformation of the protoplasts followed by regeneration of the cell wall in a manner known per se. The use of *Aspergillus* as a host micro-organism is described in EP 238 023 (Novo Nordisk), the contents of which are hereby incorporated by reference.

Method of Producing an Alpha-Amylase Variant of the Invention

In a yet further aspect, the present invention relates to a method of producing an alpha-amylase variant of the invention, which method comprises cultivating a host cell under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Starch Conversion

The present invention provides a method of using alpha-amylase variants of the invention for producing glucose or maltose or the like from starch.

Generally, the method includes the steps of partially hydrolyzing precursor starch in the presence of alpha-amylase and then further hydrolyzing the release of D-glucose from the non-reducing ends of the starch or related oligo- and polysaccharide molecules in the presence of glucoamylase by cleaving alpha-(1⊗4) and alpha-(1⊗6) glucosidic bonds.

The partial hydrolysis of the precursor starch utilizing alpha-amylase provides an initial breakdown of the starch molecules by hydrolyzing internal alpha-(1⊗4)-linkages. In commercial applications, the initial hydrolysis using alpha-amylase is run at a temperature of approximately 105° C. A very high starch concentration is processed, usually 30% to 40% solids. The initial hydrolysis is usually carried out for five minutes at this elevated temperature. The partially hydrolyzed starch can then be transferred to a second tank and incubated for approximately one hour at a temperature of 85° to 90° C. to derive a dextrose equivalent (D.E.) of 10 to 15.

The step of further hydrolyzing the release of D-glucose from the non-reducing ends of the starch or related oligo- and polysaccharides molecules in the presence of glucoamylase is normally carried out in a separate tank at a reduced temperature between 30° and 60° C. Preferably the temperature of the substrate liquid is dropped to between 55° and 60° C. The pH of the solution is dropped from 6 to 6.5 to a range between 3 and 5.5. Preferably, the pH of the solution is 4 to 4.5. The glucoamylase is added to the solution and the reaction is carried out for 24-72 hours, preferably 36-48 hours.

By improving the thermo stability of the Fungamyl-like alpha-amylase variant according to the invention said alpha-amylases may be used for starch liquefaction.

In an aspect the invention relates to the use of an alpha-amylase variant of the invention in a starch conversion process.

Brewing

The alpha-amylase variant of the invention may also be used in brewing processes.

High Maltose Syrup Production (55% Maltose)

A variant of the invention may be used for maltose production. High maltose syrup is typically produced as follows:

Production of High Maltose Syrup (containing 50-55% maltose)

To produce "High Maltose Syrup" starch is liquefied to DE 10-20. The pH and temperature of the liquefied starch is adjusted to 65° C. and to a pH around 5.0, respectively, and is subjected to maltogenic alpha-amylase activity (e.g., *Bacillus stearothermophilus* amylase, such as Maltogenase™ 4000 L, 0.4 l/t DS (Novo Nordisk)), pullulanase activity (e.g., *Bacillus pullulanase*, such as Promozyme™ 600 L, 0.3 l/t DS (Novo Nordisk)) and alpha-amylase activity (e.g., BAN 240 L or Termamyl™ 120 L, type LS, 0.4 kg/t DS (Novo Nordisk)) for 24-41 hours. The specific process time depends on the desired saccharide spectrum to be achieved. By increasing the dosage of the maltogenic alpha-amylase and pullulanase the maltose content can be increased.

Alternatively, "High Maltose Syrup" may be produced by first liquefying starch to DE 10-20 and then adjusting the pH and temperature to 55° C. and a pH around 5.5, respectively, and subjecting the liquefied starch to a fungal alpha-amylase activity (e.g., *Bacillus stearothermophilus* amylase, such as Fungamyl™ 800L (Novo Nordisk)) for 22-44 hours. The dosage of fungal alpha-amylase depends on the saccharification time foreseen, e.g., 200 g/t DS for 44 hours and 400 g/t DS for 22 hours.

To produce "High Maltose Syrup" starch with maltose content of 55-65% starch is liquefied to DE 10-20. The pH and temperature of the liquefied starch is adjusted to 60° C. and to a pH around 6, respectively, and is subjected to maltogenic alpha-amylase activity (e.g., Maltogenase™ 4000 L, 0.25-1.0 l/t DS (Novo Nordisk)), and fungal alpha-amylase activity (e.g., *Aspergillus* amylase, such as Fungamyl™ 800 L, 0.4-1.0 kg/t DS (Novo Nordisk) for 24-48 hours.

Alternatively, the liquefied starch may adjusted to a temperature of 65° C. and a pH around 5.0 and subjected to maltogenic alpha-amylase activity (e.g., *Bacillus stearothermophilus* amylase, such as Maltogenase™ 4000 L, 0.5-1.0 l/t DS), and pullulanase activity (e.g., *Bacillus pullulanase*, such as Promozyme™ 600 L, 0.5-1.0 l/t DS) for 18-42 hours.

According to the invention one or more Fungamyl-like variants of the invention may be used instead of or together with the above mentioned fungal alpha-amylase activity.

Baking

The alpha-amylase variant of the invention may also be used in baking processes.

Use

In one aspect the invention relates to the used of a variant of the invention for starch conversion, alcohol production, brewing, baking.

Processes of the Invention

The invention also relates to a process of producing maltose syrup comprising the steps of:

1) liquefying starch in the presence of an alpha-amylase;
2) dextrinization in the presence of a fungal alpha-amylase variant of the invention; and
3) recovery of the syrup; and optional purification of the syrup.

The alpha-amylase used for liquefaction in step 1) may be any alpha-amylase. Preferred alpha-amylase are *Bacillus* alpha-amylases, such as a Termamyl-like alpha-amylase, which including the *B. licheniformis* alpha-amylase (commercially available as Termamyl™ (Novo Nordisk)), the *B. amyloliquefaciens* alpha-amylase (sold as BAN (Novo Nordisk), the *B. stearothermophilus* alpha-amylase (sold as Termamyl™ 120 L type S), The alpha-amylases derived from a strain of the *Bacillus* sp. NCIB 12289, NCIB 12512, NCIB 12513 or DSM 9375, all of which are described in detail in WO 95/26397, and the alpha-amylase described by Tsukamoto et al., *Biochemical and Biophysical Research Communications*, 151 (1988), pp. 25-31. Alpha-amylases within the definition of "Termamyl-like alpha-amylase" are defined in for instance WO 96/23874 (Novo Nordisk).

In another aspect the invention relates to a process of producing maltose comprising the steps of:

1) liquefying starch at a temperature of 140-160° C. at a pH of 4-6;
2) dextrinization at a temperature in the range from 60-95° C., in particular at 65-85° C., such as 70-80° C., at a pH 4-6 in the presence of a fungal alpha-amylase variant of the invention; and
3) recovery of the syrup; and optional purification of the syrup.

In an embodiment of the invention an effective amount of glucoamylase is added in step 2). The syrup will in this embodiment (including treatment with a glucoamylase) not be maltose syrup, but syrup with a different sugar profile.

The glucoamylase may be an *Aspergillus* glucoamylase, in particular an *Aspergillus niger* glucoamylase.

Alternatively, the process comprising the steps of:
1) liquefying starch at a temperature of 95-110° C. at a pH of 4-6 in the presence of a *Bacillus* alpha-amylase;
2) liquefying at a temperature in the range from 70-95° C. at a pH 4-6 in the presence of a fungal alpha-amylase variant of the invention, followed by recovery and/or optional purification of the product obtained.

Immobilized Fungal Alpha-Amylase Variants of the Invention

In an aspect the invention relates to an immobilized alpha-amylase variant of the invention. The alpha-amylase variant may be immobilized using any suitable method know in the art such as method used for glucose isomerase in U.S. Pat. No. 4,687,742.

MATERIALS AND METHODS

Material:

Enzymes:
FUNGAMYL®: fungal alpha-amylase derived from *Aspergillus oryzae* (available from Novo Nordisk) and shown in SEQ ID NO: 2.

Host cell:
*A. oryzae* JaL125: *Aspergillus oryzae* IFO 4177 available from Institute for Fermention, Osaka; 17-25 Juso Hammachi 2-Chome Yodogawa-ku, Osaka, Japan, having the alkaline protease gene named "alp" (described by Murakami K et al., (1991), Agric. Biol. Chem. 55, p. 2807-2811) deleted by a one step gene replacement method (described by G. May in "Applied Molecular Genetics of Filamentous Fungi" (1992), p. 1-25. Eds. J. R. Kinghorn and G. Turner; Blackie Academic and Professional), using the *A. oryzae* pyrG gene as marker. Strain JaL 125 is further disclosed in WO 97/35956 (Novo Nordisk).

Micro-Organisms:
Strain: *Saccharomyces* cerevisiae YNG318: MATαleu2-Δ2 ura3-52 his4-539 pep4-Δ1[cir+]

Methods:

Transformation of *Aspergillus oryzae* (General Procedure)

100 ml of YPD (Sherman et al., (1981), Methods in Yeast Genetics, Cold Spring Harbor Laboratory) are inoculated with spores of *A. oryzae* and incubated with shaking for about 24 hours. The mycelium is harvested by filtration through miracloth and washed with 200 ml of 0.6 M $MgSO_4$. The mycelium is suspended in 15 ml of 1.2 M $MgSO_4$, 10 mM $NaH_2PO_4$, pH 5.8. The suspension is cooled on ice and 1 ml of buffer containing 120 mg of Novozym™ 234 is added. After 5 min., 1 ml of 12 mg/ml BSA (Sigma type H25) is added and incubation with gentle agitation continued for 1.5-2.5 hours at 37C until a large number of protoplasts is visible in a sample inspected under the microscope.

The suspension is filtered through miracloth, the filtrate transferred to a sterile tube and overlayed with 5 ml of 0.6 M sorbitol, 100 mM Tris-HCl, pH 7.0. Centrifugation is performed for 15 min. at 1000 g and the protoplasts are collected from the top of the $MgSO_4$ cushion. 2 volumes of STC (1.2 M sorbitol, 10 mM Tris-HCl, pH 7.5, 10 mM $CaCl_2$) are added to the protoplast suspension and the mixture is centrifugated for 5 min. at 1000 g. The protoplast pellet is resuspended in 3 ml of STC and repelleted. This is repeated. Finally, the protoplasts are resuspended in 0.2-1 ml of STC.

100 micro liter of protoplast suspension are mixed with 5-25 micro grams of p3SR2 (an *A. niulans* amdS gene carrying plasmid described in Hynes et al., Mol. and Cel. Biol., Vol. 3, No. 8, 1430-1439, August 1983) in 10 micro liter of STC. The mixture is left at room temperature for 25 minutes 0.2 ml of 60% PEG 4000 (BDH 29576), 10 mM $CaCl_2$ and 10 mM Tris-HCl, pH 7.5 is added and carefully mixed (twice) and finally 0.85 ml of the same solution are added and carefully mixed. The mixture is left at room temperature for 25 min., spun at 2.500 g for 15 min. and the pellet is resuspended in 2 ml of 1.2M sorbitol. After one more sedimentation the protoplasts are spread on minimal plates (Cove, (1966), Biochem. Biophys. Acta 113, 51-56) containing 1.0 M sucrose, pH 7.0, 10 mM acetamide as nitrogen source and 20 mM CsCl to inhibit background growth. After incubation for 4-7 days at 37C spores are picked, suspended in sterile water and spread for single colonies. This procedure is repeated and spores of a single colony after the second re-isolation are stored as a defined transformant.

Fed Batch Fermentation

Fed batch fermentation is performed in a medium comprising maltodextrin as a carbon source, urea as a nitrogen source and yeast extract. The fed batch fermentation is performed by inoculating a shake flask culture of *A. oryzae* host cells in question into a medium comprising 3.5% of the carbon source and 0.5% of the nitrogen source. After 24 hours of cultivation at pH 5.0 and 34° C. the continuous supply of additional carbon and nitrogen sources are initiated. The carbon source is kept as the limiting factor and it is secured that oxygen is present in excess. The fed batch cultivation is continued for 4 days, after which the enzymes can be recovered by centrifugation, ultrafiltration, clear filtration and germ filtration. Further purification may be done by anion-exchange chromatographic methods known in the art.

Purification

The culture broth is filtrated and added ammonium sulphate (AMS) to a concentration of 1.7 M AMS and pH is adjusted to pH 5. Precipitated material is removed by centrifugation on the solution containing alpha-amylase activity is applied on a Toyo Pearl Butyl column previously equilibrated in 1.7 M AMS, 20 mM sodium acetate, pH 5. Unbound material is washed out with the equilibration buffer. Bound proteins are eluted with 10 mM sodium acetate, pH 4.5 using a linear gradient from 1.7-0 M AMS over 10 column volumes. Glucoamylase containing fractions are collected ad dialysed against 20 mM sodium acetate, pH 4.5.

Screening for Thermostable Alpha-Amylase Variants

The libraries are screened in the thermostable filter assay described below.

Filter Assay for Thermostability

Yeast libraries are plated on a sandwich of cellulose acetate (OE 67, Schleicher & Schuell, Dassel, Germany)—and nitrocellulose filters (Protran-Ba 85, Schleicher & Schuell, Dassel, Germany) on SC ura-agar plates with 100 micro gram/ml ampicillin at 30° C. for at least 72 hrs. The colonies are replica plated to PVDF filters (Immobilon-P, Millipore, Bedford) activated with methanol for 1 min and subsequently washed in 0.1 M NaAc and then incubated at room temperature for 2 hours. Colonies are washed from PVDF filters with tap water. Each filter sandwiches and PVDF filters are specifically marked with a needle before incubation in order to be able to localise positive variants on the filters after the screening. The PVDF filters with bound variants are transferred to a container with 0.1 M NaAc, pH 4.5 and incubated at 47° C. for 15 minutes. The sandwich of cellulose acetate and nitrocellulose filters on SC ura-agar plates are stored at room temperature until use. After incubation, the residual activities are detected on plates containing 5% maltose, 1% agarose, 50 mM NaAc, pH 4.5. The assay plates with PVDF filters are marked the same way as the filter sandwiches and incubated for 2 hrs. at 50° C. After removal of the PVDF filters, the assay plates are stained with Glucose GOD perid (Boehringer Mannheim GmbH, Germany). Variants with residual activity are detected on assay plates as dark green spots on white background. The improved variants are located on the storage plates. Improved variants are re-screened twice under the same conditions as the first screen.

Determination of FAU Activity

One Fungal Alpha-Amylase Unit (FAU) is defined as the amount of enzyme, which breaks down 5.26 g starch (Merck Amylum solubile Erg. B.6, Batch 9947275) per hour at Novo Nordisk's standard method for determination of alpha-amylase based upon the following standard conditions:

Substrate . . . Soluble starch

Temperature . . . 37° C.

PH . . . 4.7

Reaction time . . . 7-20 minutes

A detailed description of Novo Nordisk's method is available on request.

Determination of Acid Alpha-Amylase Activity (AFAU)

Acid alpha-amylase activity is measured in AFAU (Acid Fungal Alpha-amylase Units), which are determined relative to an enzyme standard.

The standard used is AMG 300 L (from Novo Nordiks). The neutral alpha-amylase in this AMG falls after storage at room temperature for 3 weeks from approx. 1 FAU/mL to below 0.05 FAU/mL.

The acid alpha-amylase activity in this AMG standard is determined in accordance with AF 9 1/3 (Novo method for the determination of fungal alpha-amylase). In this method, 1 FAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

$$\text{Starch} + \text{Iodine} \xrightarrow[40° C., pH 2.5]{\text{Alpha-amylase}} \text{Dextrins} + \text{Oligosaccharides}$$

Blue/violet t=23 sec. Decoloration

Standard Conditions/Reaction Conditions: (Per Minute)
Substrate: starch, approx. 0.17 g/L
Buffer: Citate, approx. 0.03 M
Iodine ($I_2$): 0.03 g/L
$CaCl_2$: 1.85 mM
pH: 2.50 ±0.05
Incubation temperature: 40° C.
Reaction time: 23 seconds
Wavelength: lambda=590 nm
Enzyme concentration: 0.025 AFAU/mL
Enzyme working range: 0.01-0.04 AFAU/mL Further details can be found in EB-SM-0259.02/01 available on request from Novo Nordisk, and incorporated by reference.

Thermal/pH Stability Determination of Variant of the Invention

The thermal stability of variants of the invention is tested using the following method: 950 micro liter 0.1 M Citrate+ 4.3 mM $Ca^{2+}$buffer is incubated for 1 hour at 60° C. 50 micro liter enzyme in buffer (4 AFAU/ml) is added. 2×40 micro liter samples are taken at 0 and 60 minutes and chilled on ice. The activity (AFAU/ml) measured before incubation (0 minutes) is used as reference (100%). The decline in percent is calculated as a function of the incubation time.

To determine the Thermal stability the test is repeated using different temperatures, for instance 50, 60, 70, 80 and 90° C.

To determine the pH stability the test is repeated using different pHs, for instance, pH 2.5; 3; 3.5; 4; 4.5; 5.

General Method for Random Mutagenesis by Use of the DOPE Program

The random mutagenesis may be carried out as follows:
1. Select regions of interest for modification in the parent enzyme,
2. Decide on mutation sites and non-mutated sites in the selected region,
3. Decide on which kind of mutations should be carried out, e.g. with respect to the desired stability and/or performance of the variant to be constructed,
4. Select structurally reasonable mutations,
5. Adjust the residues selected by step 3 with regard to step 4.
6. Analyze by use of a suitable dope algorithm the nucleotide distribution.
7. If necessary, adjust the wanted residues to genetic code realism, e.g., taking into account constraints resulting from the genetic code, e.g., in order to avoid introduction of stop codons; the skilled person will be aware that some codon combinations cannot be used in practice and will need to be adapted
8. Make primers
9. Perform random mutagenesis by use of the primers
10. Select resulting glucoamylase variants by screening for the desired improved properties.

Dope Algorithm

Suitable dope algorithms for use in step 6 are well known in the art. One such algorithm is described by Tomandl, D. et al., 1997, Journal of Computer-Aided Molecular Design 11:29-38. Another algorithm is DOPE (Jensen, L J, Andersen, K V, Svendsen, A, and Kretzschmar, T (1998) Nucleic Acids Research 26:697-702).

EXAMPLES

Example 1

Construction of variant Q153S

For the construction of variants of the TAKA-amylase enzyme (Fungamyl™ shown in SEQ ID NOS: 1 and 2) the commercial kit, Chameleon double-stranded, site-directed mutagenesis kit is used according to the manufacturer's instructions.

The gene encoding the amylase enzyme in question is in plasmid pTAKA17 (EP 238,023, figure 2 and Example 2). In accordance with the manufacturer's instructions the ScaI site of the Ampicillin gene of pTAKA17 is changed to a MluI site by use of the following primer:

Primer 7258:
5'p gaa tga ctt ggt tga cgc gtc acc agt cac 3' (SEQ ID NO: 3)

The ScaI site in an intron in the Amylase gene is removed using the primer

Primer 1:
5'p ATG GTT CAT TTC AGA ACT GAC ATT GAG TAA (SEQ ID NO: 4)

The desired mutation is introduced into the amylase gene in question by addition of an appropriate oligos comprising the desired mutation.

To introduce a mutation such as Q153S an oligo is design:

Primer 2:
5'P TTC TGT TTC ATT TCG AAC TAT GAA GAT (SEQ ID NO: 5)

The pTAKA17 vector comprising the amylase gene in question is then used as a template for DNA polymerase, DNA ligase (for ligation to 5'Phosphate (5'P) on the oligoes), and the oligoes 7258, primer 1 and primer 2.

DNA-prep. are made, and the introduction of the mutation is verified by sequencing.

The DNA prep. is transformed in *Aspergillus oryzae* host cell as describe in the "Materials & Methods" section and the transformants are screened for amylase activity.

Example 2

Increased Thermo Stability

The variant constructed in Example 1 is tested for increased thermostability in accordance with the thermo stability determination assay disclosed in the "Materials & Methods" section.

Example 3

Increased Acidic Stability

The variant constructed in Example 1 is tested for increased stability at acidic pH in accordance with the pH stability determination assay disclosed in the "Materials & Methods" section.

---

The invention claimed is:

1. A variant of a parent Fungamyl-like alpha-amylase, comprising an alteration at one or more regions selected from the group consisting of region 98-110 and region 161-167, wherein (a) the alteration(s) are independently
   (i) an insertion of an amino acid downstream of the amino acid which occupies the position,
   (ii) a deletion of the amino acid which occupies the position, or
   (iii) a substitution of the amino acid which occupies the position with a different amino acid, (b) the variant has alpha-amylase activity; (c) each region or position corresponds to a region or position of the amino acid sequence of the parent Fungamyl-like alpha-amylase having the amino acid sequence of SEQ ID NO: 2 and (d) wherein the parent Fungamyl-like alpha-amylase is an alpha-amylase from *Aspergillus niger*.

2. The variant of claim 1, wherein the variant further includes a substitution: Q153S.

3. The variant of claim 1, wherein the variant has improved thermostability or increased stability at acidic pH or improved thermostability and increased stability at acidic pH.

4. A composition for producing high maltose syrup comprising the variant of claim 1.

5. A dough improving composition, comprising the variant of claim 1.

6. A brewing composition, comprising the variant of claim 1.

7. The brewing composition of claim 6, further comprising at least one additional enzyme wherein the additional enzyme is a beta-amylase or an isoamylase.

8. A composition for producing alcohol, comprising the variant of claim 1.

9. The variant of claim 1 wherein the variant is immobilized.

10. The variant of claim 1, wherein the alteration is an alteration in Region 98-110.

11. The variant of claim 1, wherein the alteration is an alteration in Region 161-167.

12. The variant of claim 1, wherein the variant comprises an alteration at a position corresponding to position 98 in SEQ ID NO:2.

13. The variant of claim 1, wherein the variant comprises an alteration at a position corresponding to position 99 in SEQ ID NO:2.

14. The variant of claim 1, wherein the variant comprises an alteration at a position corresponding to position 100 in SEQ ID NO:2.

15. The variant of claim 1, wherein the variant comprises an alteration at a position corresponding to position 101 in SEQ ID NO:2.

16. The variant of claim 1, wherein the variant comprises an alteration at a position corresponding to position 102 in SEQ ID NO:2.

17. The variant of claim 1, wherein the variant comprises an alteration at a position corresponding to position 103 in SEQ ID NO:2.

18. The variant of claim 1, wherein the variant comprises an alteration at a position corresponding to position 104 in SEQ ID NO:2.

19. The variant of claim 1, wherein the variant comprises an alteration at a position corresponding to position 105 in SEQ ID NO:2.

20. The variant of claim 1, wherein the variant comprises an alteration at a position corresponding to position 106 in SEQ ID NO:2.

21. The variant of claim 1, wherein the variant comprises an alteration at a position corresponding to position 107 in SEQ ID NO:2.

22. The variant of claim 1, wherein the variant comprises an alteration at a position corresponding to position 108 in SEQ ID NO:2.

23. The variant of claim 1, wherein the variant comprises an alteration at a position corresponding to position 109 in SEQ ID NO:2.

24. The variant of claim 1, wherein the variant comprises an alteration at a position corresponding to position 110 in SEQ ID NO:2.

25. The variant of claim 1, wherein the variant comprises an alteration at a position corresponding to position 161 in SEQ ID NO:2.

26. The variant of claim 1, wherein the variant comprises an alteration at a position corresponding to position 162 in SEQ ID NO:2.

27. The variant of claim 1, wherein the variant comprises an alteration at a position corresponding to position 163 in SEQ ID NO:2.

28. The variant of claim 1, wherein the variant comprises an alteration at a position corresponding to position 164 in SEQ ID NO:2.

29. The variant of claim 1, wherein the variant comprises an alteration at a position corresponding to position 165 in SEQ ID NO:2.

30. The variant of claim 1, wherein the variant comprises an alteration at a position corresponding to position 166 in SEQ ID NO:2.

31. The variant of claim 1, wherein the variant comprises an alteration at a position corresponding to position 167 in SEQ ID NO:2.

* * * * *

SEQUENCE LISTING

```
<160> NUMBER OF SEQ ID NOS: 5

<210> SEQ ID NO 1
<211> LENGTH: 1734
<212> TYPE: DNA
<213> ORGANISM: Aspergillus Oryzae
<220> FEATURE:
<221> NAME/KEY: CDS
<222> LOCATION: (54)..(1547)
<223> OTHER INFORMATION: mat_peptide
<220> FEATURE:
<221> NAME/KEY: mat_peptide
<222> LOCATION: (114)..(1733)

<400> SEQUENCE: 1
tcacatcaag ctctcccttc tctgaacaat aaacccaca gaaggcattt atg atg       56
                                                          Met
                                                          -20 gtc gcg tgg tgg tct cta ttt ctg tac ggc ctt cag gtc gcg gca cct    104
Val Ala Trp Trp Ser Leu Phe Leu Tyr Gly Leu Gln Val Ala Ala Pro
            -15                 -10                 -5 gct ttg gct gca acg cct gcg gac tgg cga tcg caa tcc att tat ttc    152
Ala Leu Ala Ala Thr Pro Ala Asp Trp Arg Ser Gln Ser Ile Tyr Phe
    -1  1                 5                  10 ctt ctc acg gat cga ttt gca agg acg gat ggg tcg acg act gcg act    200
Leu Leu Thr Asp Arg Phe Ala Arg Thr Asp Gly Ser Thr Thr Ala Thr
        15                  20                  25 tgt aat act gcg gat cag aaa tac tgt ggt gga aca tgg cag ggc atc    248
Cys Asn Thr Ala Asp Gln Lys Tyr Cys Gly Gly Thr Trp Gln Gly Ile
30                  35                  40                  45
```

-continued

```
atc gac aag ttg gac tat atc cag gga atg ggc ttc aca gcc atc tgg      296
Ile Asp Lys Leu Asp Tyr Ile Gln Gly Met Gly Phe Thr Ala Ile Trp
         50                  55                  60 atc acc ccc gtt aca gcc cag ctg ccc cag acc acc gca tat gga gat      344
Ile Thr Pro Val Thr Ala Gln Leu Pro Gln Thr Thr Ala Tyr Gly Asp
 65                  70                  75 gcc tac cat ggc tac tgg cag cag gat ata tac tct ctg aac gaa aac      392
Ala Tyr His Gly Tyr Trp Gln Gln Asp Ile Tyr Ser Leu Asn Glu Asn
             80                  85                  90 tac ggc act gca gat gac ttg aag gcg ctc tct tcg gcc ctt cat gag      440
Tyr Gly Thr Ala Asp Asp Leu Lys Ala Leu Ser Ser Ala Leu His Glu
 95                 100                 105 agg ggg atg tat ctt atg gtc gat gtg gtt gct aac cat atg ggc tat      488
Arg Gly Met Tyr Leu Met Val Asp Val Val Ala Asn His Met Gly Tyr
110                 115                 120                 125 gat gga gcg ggt agc tca gtc gat tac agt gtg ttt aaa ccg ttc agt      536
Asp Gly Ala Gly Ser Ser Val Asp Tyr Ser Val Phe Lys Pro Phe Ser
                130                 135                 140 tcc caa gac tac ttc cac ccg ttc tgt ttc att caa aac tat gaa gat      584
Ser Gln Asp Tyr Phe His Pro Phe Cys Phe Ile Gln Asn Tyr Glu Asp
                    145                 150                 155 cag act cag gtt gag gat tgc tgg cta gga gat aac act gtc tcc ttg      632
Gln Thr Gln Val Glu Asp Cys Trp Leu Gly Asp Asn Thr Val Ser Leu
                        160                 165                 170 cct gat ctc gat acc acc aag gat gtg gtc aag aat gaa tgg tac gac      680
Pro Asp Leu Asp Thr Thr Lys Asp Val Val Lys Asn Glu Trp Tyr Asp
175                 180                 185 tgg gtg gga tca ttg gta tcg aac tac tcc att gac ggc ctc cgt atc      728
Trp Val Gly Ser Leu Val Ser Asn Tyr Ser Ile Asp Gly Leu Arg Ile
190                 195                 200                 205 gac aca gta aaa cac gtc cag aag gac ttc tgg ccc ggg tac aac aaa      776
Asp Thr Val Lys His Val Gln Lys Asp Phe Trp Pro Gly Tyr Asn Lys
                    210                 215                 220 gcc gca ggc gtg tac tgt atc ggc gag gtg ctc gac ggt gat ccg gcc      824
Ala Ala Gly Val Tyr Cys Ile Gly Glu Val Leu Asp Gly Asp Pro Ala
                        225                 230                 235 tac act tgt ccc tac cag aac gtc atg gac ggc gta ctg aac tat ccc      872
Tyr Thr Cys Pro Tyr Gln Asn Val Met Asp Gly Val Leu Asn Tyr Pro
                            240                 245                 250 att tac tat cca ctc ctc aac gcc ttc aag tca acc tcc ggc agc atg      920
Ile Tyr Tyr Pro Leu Leu Asn Ala Phe Lys Ser Thr Ser Gly Ser Met
255                 260                 265 gac gac ctc tac aac atg atc aac acc gtc aaa tcc gac tgt cca gac      968
Asp Asp Leu Tyr Asn Met Ile Asn Thr Val Lys Ser Asp Cys Pro Asp
270                 275                 280                 285 tca aca ctc ctg ggc aca ttc gtc gag aac cac gac aac cca cgg ttc     1016
Ser Thr Leu Leu Gly Thr Phe Val Glu Asn His Asp Asn Pro Arg Phe
                    290                 295                 300 gct tct tac acc aac gac ata gcc ctc gcc aag aac gtc gca gca ttc     1064
Ala Ser Tyr Thr Asn Asp Ile Ala Leu Ala Lys Asn Val Ala Ala Phe
                        305                 310                 315 atc atc ctc aac gac gga atc ccc atc atc tac gcc ggc caa gaa cag     1112
Ile Ile Leu Asn Asp Gly Ile Pro Ile Ile Tyr Ala Gly Gln Glu Gln
                            320                 325                 330 cac tac gcc ggc gga aac gac ccc gcg aac cgc gaa gca acc tgg ctc     1160
His Tyr Ala Gly Gly Asn Asp Pro Ala Asn Arg Glu Ala Thr Trp Leu
335                 340                 345 tcg ggc tac ccg acc gac agc gag ctg tac aag tta att gcc tcc gcg     1208
Ser Gly Tyr Pro Thr Asp Ser Glu Leu Tyr Lys Leu Ile Ala Ser Ala
350                 355                 360                 365
```

-continued

```
aac gca atc cgg aac tat gcc att agc aaa gat aca gga ttc gtg acc      1256
Asn Ala Ile Arg Asn Tyr Ala Ile Ser Lys Asp Thr Gly Phe Val Thr
            370                 375                 380 tac aag aac tgg ccc atc tac aaa gac gac aca acg atc gcc atg cgc      1304
Tyr Lys Asn Trp Pro Ile Tyr Lys Asp Asp Thr Thr Ile Ala Met Arg
        385                 390                 395 aag ggc aca gat ggg tcg cag atc gtg act atc ttg tcc aac aag ggt      1352
Lys Gly Thr Asp Gly Ser Gln Ile Val Thr Ile Leu Ser Asn Lys Gly
    400                 405                 410 gct tcg ggt gat tcg tat acc ctc tcc ttg agt ggt gcg ggt tac aca      1400
Ala Ser Gly Asp Ser Tyr Thr Leu Ser Leu Ser Gly Ala Gly Tyr Thr
415                 420                 425 gcc ggc cag caa ttg acg gag gtc att ggc tgc acg acc gtg acg gtt      1448
Ala Gly Gln Gln Leu Thr Glu Val Ile Gly Cys Thr Thr Val Thr Val
430                 435                 440                 445 ggt tcg gat gga aat gtg cct gtt cct atg gca ggt ggg cta cct agg      1496
Gly Ser Asp Gly Asn Val Pro Val Pro Met Ala Gly Gly Leu Pro Arg
            450                 455                 460 gta ttg tat ccg act gag aag ttg gca ggt agc aag atc tgt agt agc      1544
Val Leu Tyr Pro Thr Glu Lys Leu Ala Gly Ser Lys Ile Cys Ser Ser
        465                 470                 475 tcg tgaagggtgg agagtatatg atggtactgc tattcaatct ggcattggac           1597
Ser agtgagtttg agtttgatgt acagttggag tcgttactgc tgtcatcccc ttatactctt    1657
cgattgtttt tcgaacccta atgccaagca cgctagtcta ttataggaaa aaaaaaaaa     1717 aaaaaaaaaa aaaaaa                                                    1734

<210> SEQ ID NO 2
<211> LENGTH: 498
<212> TYPE: PRT
<213> ORGANISM: Aspergillus Oryzae

<400> SEQUENCE: 2

Met Val Ala Trp Trp Ser Leu Phe Leu Tyr Gly Leu Gln Val Ala Ala
-20              -15                 -10                  -5

Pro Ala Leu Ala Ala Thr Pro Ala Asp Trp Arg Ser Gln Ser Ile Tyr
         -1  1              5                  10

Phe Leu Leu Thr Asp Arg Phe Ala Arg Thr Asp Gly Ser Thr Thr Ala
            15                  20                  25

Thr Cys Asn Thr Ala Asp Gln Lys Tyr Cys Gly Gly Thr Trp Gln Gly
        30                  35                  40

Ile Ile Asp Lys Leu Asp Tyr Ile Gln Gly Met Gly Phe Thr Ala Ile
45                  50                  55                  60

Trp Ile Thr Pro Val Thr Ala Gln Leu Pro Gln Thr Thr Ala Tyr Gly
                65                  70                  75

Asp Ala Tyr His Gly Tyr Trp Gln Gln Asp Ile Tyr Ser Leu Asn Glu
            80                  85                  90

Asn Tyr Gly Thr Ala Asp Asp Leu Lys Ala Leu Ser Ser Ala Leu His
        95                  100                 105

Glu Arg Gly Met Tyr Leu Met Val Asp Val Val Ala Asn His Met Gly
    110                 115                 120

Tyr Asp Gly Ala Gly Ser Ser Val Asp Tyr Ser Val Phe Lys Pro Phe
125                 130                 135                 140

Ser Ser Gln Asp Tyr Phe His Pro Phe Cys Phe Ile Gln Asn Tyr Glu
                145                 150                 155
```

```
Asp Gln Thr Gln Val Glu Asp Cys Trp Leu Gly Asp Asn Thr Val Ser
            160                 165                 170

Leu Pro Asp Leu Asp Thr Thr Lys Asp Val Val Lys Asn Glu Trp Tyr
        175                 180                 185

Asp Trp Val Gly Ser Leu Val Ser Asn Tyr Ser Ile Asp Gly Leu Arg
    190                 195                 200

Ile Asp Thr Val Lys His Val Gln Lys Asp Phe Trp Pro Gly Tyr Asn
205                 210                 215                 220

Lys Ala Ala Gly Val Tyr Cys Ile Gly Glu Val Leu Asp Gly Asp Pro
                225                 230                 235

Ala Tyr Thr Cys Pro Tyr Gln Asn Val Met Asp Gly Val Leu Asn Tyr
            240                 245                 250

Pro Ile Tyr Tyr Pro Leu Leu Asn Ala Phe Lys Ser Thr Ser Gly Ser
            255                 260                 265

Met Asp Asp Leu Tyr Asn Met Ile Asn Thr Val Lys Ser Asp Cys Pro
        270                 275                 280

Asp Ser Thr Leu Leu Gly Thr Phe Val Glu Asn His Asp Asn Pro Arg
285                 290                 295                 300

Phe Ala Ser Tyr Thr Asn Asp Ile Ala Leu Ala Lys Asn Val Ala Ala
                305                 310                 315

Phe Ile Ile Leu Asn Asp Gly Ile Pro Ile Ile Tyr Ala Gly Gln Glu
            320                 325                 330

Gln His Tyr Ala Gly Gly Asn Asp Pro Ala Asn Arg Glu Ala Thr Trp
            335                 340                 345

Leu Ser Gly Tyr Pro Thr Asp Ser Glu Leu Tyr Lys Leu Ile Ala Ser
        350                 355                 360

Ala Asn Ala Ile Arg Asn Tyr Ala Ile Ser Lys Asp Thr Gly Phe Val
365                 370                 375                 380

Thr Tyr Lys Asn Trp Pro Ile Tyr Lys Asp Asp Thr Thr Ile Ala Met
                385                 390                 395

Arg Lys Gly Thr Asp Gly Ser Gln Ile Val Thr Ile Leu Ser Asn Lys
            400                 405                 410

Gly Ala Ser Gly Asp Ser Tyr Thr Leu Ser Leu Ser Gly Ala Gly Tyr
        415                 420                 425

Thr Ala Gly Gln Gln Leu Thr Glu Val Ile Gly Cys Thr Thr Val Thr
    430                 435                 440

Val Gly Ser Asp Gly Asn Val Pro Val Pro Met Ala Gly Gly Leu Pro
445                 450                 455                 460

Arg Val Leu Tyr Pro Thr Glu Lys Leu Ala Gly Ser Lys Ile Cys Ser
                465                 470                 475

Ser Ser
```

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
gaatgacttg gttgacgcgt caccagtcac                                    30

<210> SEQ ID NO 4
<211> LENGTH: 30
<212> TYPE: DNA
<213> ORGANISM: Artificial Sequence

```
<220> FEATURE:
<223> OTHER INFORMATION: Primer

<400> SEQUENCE: 4
atggttcatt tcagaactga cattgagtaa                                              30

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
ttctgtttca tttcgaacta tgaagat                                                 27
```